(12) United States Patent
Spinelli et al.

(10) Patent No.: US 7,698,927 B2
(45) Date of Patent: Apr. 20, 2010

(54) METHODS AND SYSTEMS FOR MEASURING ATMOSPHERIC WATER CONTENT

(75) Inventors: Charles B. Spinelli, Bainbridge Island, WA (US); Brian J. Tillotson, Kent, WA (US); Tamaira E. Ross, Seattle, WA (US)

(73) Assignee: The Boeing Company, Chicago, IL (US)

( * ) Notice: Subject to any disclaimer, the term of this patent is extended or adjusted under 35 U.S.C. 154(b) by 425 days.

(21) Appl. No.: 11/668,956

(22) Filed: Jan. 30, 2007

(65) Prior Publication Data
US 2008/0178659 A1    Jul. 31, 2008

(51) Int. Cl.
*G01N 7/00* (2006.01)
(52) U.S. Cl. .................................... 73/29.01
(58) Field of Classification Search ................ 73/29.01
See application file for complete search history.

(56) References Cited

U.S. PATENT DOCUMENTS

| | | | |
|---|---|---|---|
| 3,369,361 A * | 2/1968 | Craig | ..................... 60/39.5 |
| 4,028,942 A | 6/1977 | Gardiner | |
| 4,674,463 A * | 6/1987 | Duckworth et al. | ........... 60/278 |
| 6,563,452 B1 * | 5/2003 | Zheng et al. | ............... 342/26 R |
| 6,937,937 B1 | 8/2005 | Manfred et al. | |
| 6,943,699 B2 | 9/2005 | Ziarno | |
| 6,977,608 B1 | 12/2005 | Anderson et al. | |
| 7,069,147 B2 | 6/2006 | Manfred et al. | |
| 7,175,136 B2 * | 2/2007 | Shah et al. | ............... 244/134 R |
| 7,213,566 B1 * | 5/2007 | Jankovic | ..................... 123/302 |
| 7,448,359 B2 * | 11/2008 | Jankovic | ..................... 123/432 |
| 2006/0155432 A1 | 7/2006 | Brown | |

FOREIGN PATENT DOCUMENTS

EP    1717553 A2    2/2006

OTHER PUBLICATIONS

International Search Report PCT/US2007/088302; Jun. 5, 2008; 44 pages.

* cited by examiner

*Primary Examiner*—Hezron Williams
*Assistant Examiner*—Rodney T Frank
(74) *Attorney, Agent, or Firm*—Armstrong Teasdale LLP

(57) ABSTRACT

Methods and systems for measuring atmospheric water content, are provided. The method includes measuring a first air temperature and a first air pressure at a first location in a compressor, measuring a second air temperature and a second air pressure at a second location in the compressor, computing a ratio of specific heats from the first and second air temperatures and the first and second air pressures, and determining an atmospheric water content from the ratio of specific heats.

17 Claims, 5 Drawing Sheets

METHODS AND SYSTEMS FOR MEASURING ATMOSPHERIC WATER CONTENT

BACKGROUND OF THE INVENTION

This invention relates generally to methods and systems for measuring atmospheric conditions and more particularly, to methods and systems for collecting atmospheric weather data using an aircraft.

An important obstacle to improved forecasting is lack of data about water content in the troposphere. Water content of an air mass can change rapidly during storms, over moist soil, or over bodies of water such as oceans. An inability to track changes in water content in these and other areas contributes to inaccurate weather forecasts.

Existing methods for detecting and quantifying water vapor are inadequate because they can only be implemented on a local scale over land thereby leaving vast gaps in global meteorological continuity. The largest gaps occur over oceans where most atmospheric conditions originate. Although the existing atmospheric sensing systems listed below exhibit high resolution capabilities on a local scale, it is not practical to deploy such systems on a global scale because they are expensive to implement or maintain on a global scale and they lack adequate temporal and/or spatial resolution for realistic use on a global scale.

Currently, a primary source of water vapor measurements are ground-based humidity sensors and balloon-borne sensors called "radiosondes." Radiosonde data have high quality, but have relatively poor spatial and temporal resolution. The radiosonde, an expendable balloon-borne instrument package that relays temperature, humidity, and pressure data to a ground receiver by radio signals, is the traditional cornerstone of the worldwide operational weather analysis and prediction system through deployments twice daily at several hundred sites around the world. However, the twice daily radiosonde deployments are primarily over land and are sparsely distributed due to cost considerations. No above-ground measurements are available during intervals between launches or at locations far from radiosonde launch points. For these reasons, radiosonde data is too costly and localized to support high resolution global meteorology.

A limited number of commercial air carriers presently provide real-time wind, pressure, temperature, and humidity readings around the world as part of a system called Aeronautical Communications Addressing and Reporting System (ACARS). Although the ACARS system provides about 10,000 readings per day world wide at a cost about 100 times less than the recurring cost of radiosondes, the vast majority of ACARS readings are around airports and along common flight paths at established cruise flight levels which limits the spatial scope of this otherwise valuable data.

Earth-based Differential Absorption Lidar (DIAL) and Raman Lidar systems are used to provide wind and water vapor profiles in remote areas. However, such systems are not economic to install and maintain, they do not penetrate cloud cover, and the lasers used are highly energized and are therefore not eye-safe.

Water vapor radiometers are instruments that measure microwave energy emitted by the atmosphere to estimate zenithal integrated water vapor. Integrated water vapor is a measure of the depth of liquid water that would result if a column of water vapor were condensed into liquid water. Zenithal integrated water vapor (IWV), also known as Precipitable Water Vapor (PWV), is the integrated water vapor in a vertical column directly overhead an Earth-based measuring device. Earth-based upward-looking water vapor radiometers estimate PWV by measuring radiative brightness temperatures against the cold background of space. However, upward-looking water vapor radiometers must be "tuned" to local conditions using independently obtained PWV data, and although they generally exhibit good temporal resolution in relatively clear atmospheric conditions, they provide only localized PWV over land. Further, unless properly equipped, upward-looking radiometers are virtually useless in rain. Alternatively, satellite-based, downward-looking radiometers perform well over water and consistent temperature land masses by viewing microwave emissions from the atmosphere and underlying Earth's surface. Although downward-looking radiometers generally exhibit good spatial resolution they exhibit poor temporal resolution and perform poorly over most land masses. In either case, water vapor radiometers as a whole are not practical for global scale meteorology due to their cost, limited view, and performance characteristics.

Fourier Transform Infrared Radiometer (FTIR) systems can provide high resolution satellite-based and Earth-based temperature and water vapor profiles by using a recursive solution of the radiative transfer equation to provide a vertical profile from the ground up. Although this method can provide vertical resolution of several hundred meters to a kilometer in the lower troposphere, the system exhibits poor performance in the presence of cloud cover and infrared active gases such as tropospheric ozone.

Unmanned Air Vehicles (UAV's) provide high resolution data in regions inaccessible to other systems discussed above. However, unmanned aircraft are too costly for continuous global sensing, they lack adequate spatial and temporal resolution, and are typically only justified in specialized research applications.

Additional water content measurements are available from satellites and from a few specially-equipped airliners operated under a NASA program called Tropospheric Airborne Meteorological Data Reporting (TAMDAR). Satellite data are unreliable because it is difficult for satellites to correctly resolve the altitude profile of moisture, especially when clouds are present. TAMDAR uses humidity sensors mounted on the outside of small, regional airliners. These sensors continuously measure humidity and temperature as the aircraft ascend and descend through the troposphere. This provides better spatial and temporal resolution than radiosondes. Though this approach has been shown to be technically effective for improved weather forecasts in the northeastern US, the additional weight and drag and the need for FAA certification of each type of sensor package on each type of aircraft makes this solution costly, which has limited the expansion of existing systems to other regions.

BRIEF DESCRIPTION OF THE INVENTION

In one embodiment, a method of measuring atmospheric water content includes measuring a first air temperature and a first air pressure at a first location in a compressor, measuring a second air temperature and a second air pressure at a second location in the compressor, computing a ratio of specific heats from the first and second air temperatures and the first and second air pressures, and determining an atmospheric water content from the ratio of specific heats.

In another embodiment, an atmospheric monitoring system includes a compressor and at least one compressor sensor coupled to the compressor, wherein the sensor is configured to acquire atmospheric data from air channeled through the compressor.

In yet another embodiment, a method of forecasting weather includes acquiring atmospheric data from a gas turbine engine onboard an aircraft during flight, processing the atmospheric data to determine an amount of water content in the atmosphere, transmitting at least one of the atmospheric data and the amount of water content to a weather forecast model, and predicting weather based on either one or both datasets.

In still another embodiment, a method of forecasting weather includes determining a specific heat of a volume of air at a first location in a gas turbine engine, determining a specific heat of the volume of air at a second location in the gas turbine engine, and determining a water content of the volume of air using the specific heat of the volume of air at the first location and the second location.

DETAILED DESCRIPTION OF THE INVENTION

Figure 1:
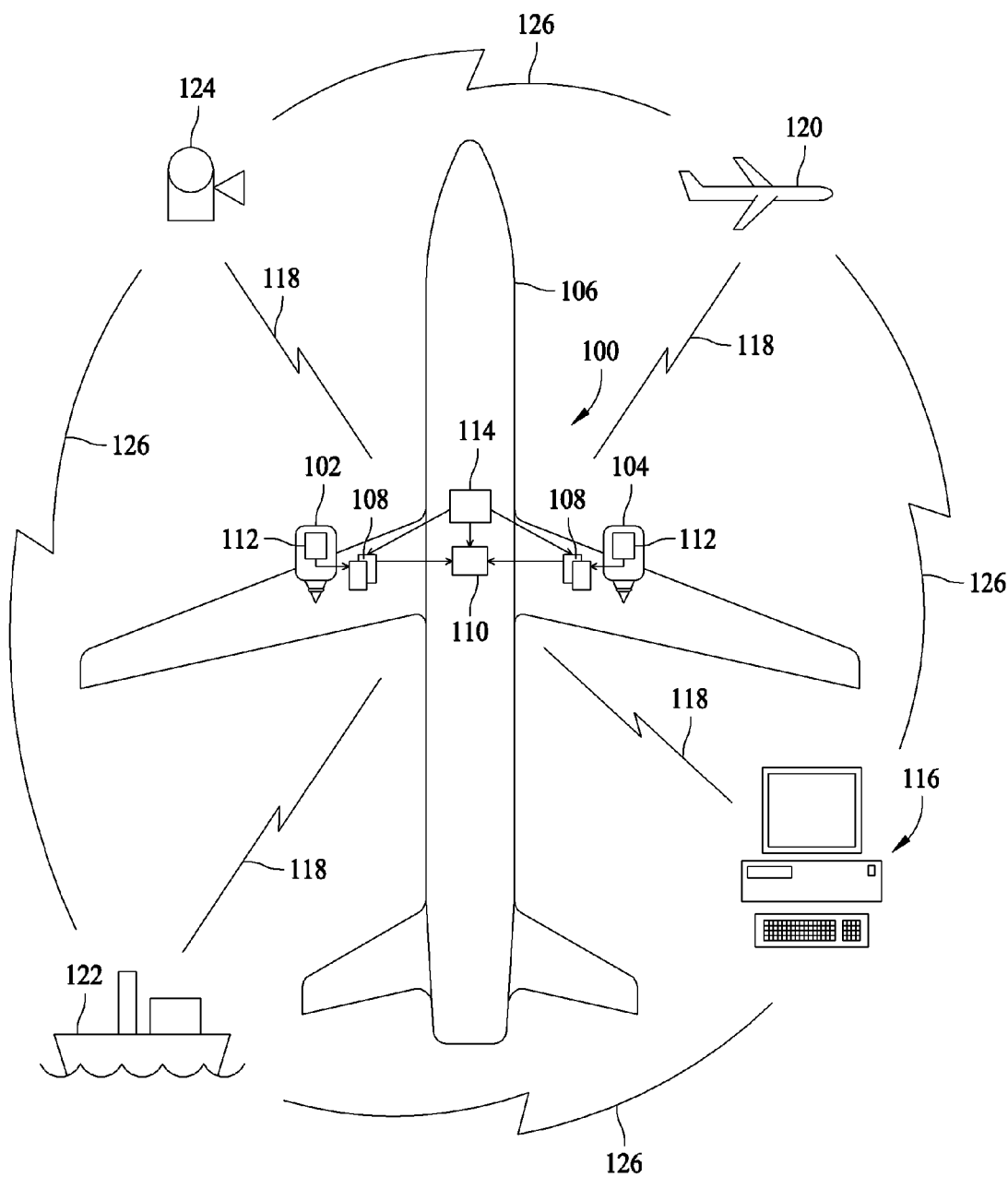
FIG. 1 is a block diagram of an exemplary embodiment of a system for collecting weather related data and monitoring the performance of gas turbine engines mounted on an aircraft.

FIG. 1 is a block diagram of an exemplary embodiment of a system 100 for collecting weather related data and monitoring the performance of gas turbine engines 102, 104 mounted on an aircraft 106. Although two engines 102 and 104 are shown in FIG. 1, it should be noted that aircraft 106 could have additional engines mounted thereon. Accordingly, data collection for such additional engines would be accomplished in a manner substantially similar to that for engines 102 and 104. Therefore, only engines 102 and 104 and the associated equipment will be described herein. Furthermore, it should be noted that the system 100 is described in connection with an aircraft only by way of example. In addition to aeronautical applications, the present invention is applicable to other applications of gas turbine engines, including marine and industrial applications.

System 100 includes an electronic engine controller (EEC) 108, such as a full authority digital engine control (FADEC), although other controllers can be used, associated with each engine 102, 104 and an onboard aircraft data storage device 110. Conventional engine data sensors 112 and aircraft data sensors 114 are provided to sense selected data parameters related to the operation and performance of engines 102, 104 and/or aircraft 106. The engine data sensors 112 and aircraft data sensors 114 can comprise any group of sensors that monitor data parameters of interest. In addition to aircraft parameters such as ambient temperature, air speed and altitude, engine parameters typically include exhaust gas temperature, oil temperature, component temperatures such as high pressure turbine shroud temperature, engine fuel flow, core speed, an engine inlet pressure (P0) and an engine inlet temperature (T12) measured upstream of the fan at the engine inlet, and a compressor discharge temperature (T3) and a compressor discharge pressure (P3) measured downstream of the engine high pressure compressor, a turbine exhaust pressure, fan speed, and other engine parameters.

Each ECU 108 receives signals from corresponding engine data sensors 112 and the aircraft data sensors 114 as is known in the art. In response to these and other inputs, ECUs 108 generate command signals to operate engine actuators, such as hydro-mechanical units (not shown) that meter the flow of fuel to respective engines 102, 104. Each ECU 108 also outputs data signals to aircraft data storage device 110. Aircraft data storage device 110, which can be any conventional device such as a flight data recorder, quick access recorder, or any other type of in-flight data storage device, has a relatively large data storage capacity for storing the data signals. Aircraft data storage device 110 could also contain processing capability to analyze data in-flight and only send the necessary maintenance messages to an aircraft centralized maintenance computer (not shown). Aircraft data storage device 110 also receives signals from aircraft data sensors 114.

System 100 includes an algorithm that processes the data signals for monitoring engine performance characteristics. The monitoring algorithm can be implemented in a number of ways. For example, the monitoring algorithm could be implemented on the ECUs 108 wherein the data signals are processed as they are received by the ECUs 108. Alternatively, the monitoring algorithm could be implemented on aircraft data storage device 110. In this case, the data signals would be processed after being transferred to aircraft data storage device 110. Another alternative is to implement the monitoring algorithm on a ground station computer 116, such as personal or workstation computer. The data signals stored in aircraft data storage device 110 during a flight are downloaded to ground station computer 116 for processing. This transfer can be accomplished after the flight via a communications link 118 including use of a removable computer-readable medium, such as a floppy disk, CD-ROM or other optical medium, magnetic tape or the like, or a multimode communication link that may include a wireless portion. It is also possible to remotely transmit the data signals directly to ground station computer 116 during flight operations for real-time processing. The signals may also be sent to other vehicles and/or facilities such as other aircraft 120, ships 122, and satellites 124 via link 118. Additionally, each of aircraft 120, ships 122, and satellites 124 may communicate between each other using separate communication links 126. A continuous and contemporaneous relaying of atmospheric information between aircraft 106, ground station computer 116, other aircraft 120, satellites 124 and ships 122, or other ocean-based vessels or structures constitutes in part an atmospheric data network accessible to a plurality of users world-wide. With any implementation, the monitoring algorithm can be stored on one unit, for example, ECU 108, aircraft data storage device 110, or ground station computer 116 and accessed from there, or alternatively, it could be accessed from a removable computer-readable medium inserted into the appropriate drive of the unit. The monitoring algorithm could also be accessed via the Internet or another computer network. As used herein, the term "computer-readable medium" refers generally to any medium from which stored data can be read by a computer or similar unit. This includes not only removable media such as the aforementioned floppy disk and CD-ROM, but also non-removable media such as a hard disk or integrated circuit memory device in each ECU 108, aircraft data storage device 110, or ground station computer 116.

Further examples of ground station computer 116 include international weather services, National Oceanic and Atmospheric Administration (NOAA), national military weather services, international military weather services such as NATO and other alliances, the national weather service, and other commercial users of weather information.

During operation, sensors 112 collect atmospheric information from at least one of engines 102, 104 and begin processing the data by, for example, transferring the data in whole or in part to ground station computer 116, other aircraft 120, satellites 124 and ships 122 to determine the atmospheric humidity conditions surrounding aircraft 106. By time and location stamping the atmospheric information at a plurality of positions along the various flight paths of the aircraft that are a part of system 100 a humidity profile of a large portion of the atmosphere can be determined. Aircraft 106 may pre-process at least a portion of the atmospheric information and may store the information on board or may transmit the information in real-time to be used by ground station computer 116, other aircraft 120, satellites 124, and ships 122.

In the exemplary embodiment, the algorithm includes the capability of continuously determining atmospheric weather parameters by using one or more of engines 102 and 104 as a sensor to derive atmospheric weather parameter values from existing aircraft engine collected data. For example, in the exemplary embodiment, engines 102 and/or 104 are used as a humidity sensor to determine an amount of atmospheric water vapor content entering the engine and therefore the amount of atmospheric water vapor content in the air surrounding aircraft 106. In the exemplary embodiment, pressure (P) and temperature (T) measurements taken from the turbine engine's inlet and compressor stages are used to determine atmospheric water vapor content. The determined water content value and a time and location at which the measurements were made are transmitted to, for example, ground station computer 116 for assimilating humidity measurements into weather forecasts.

Figure 2:
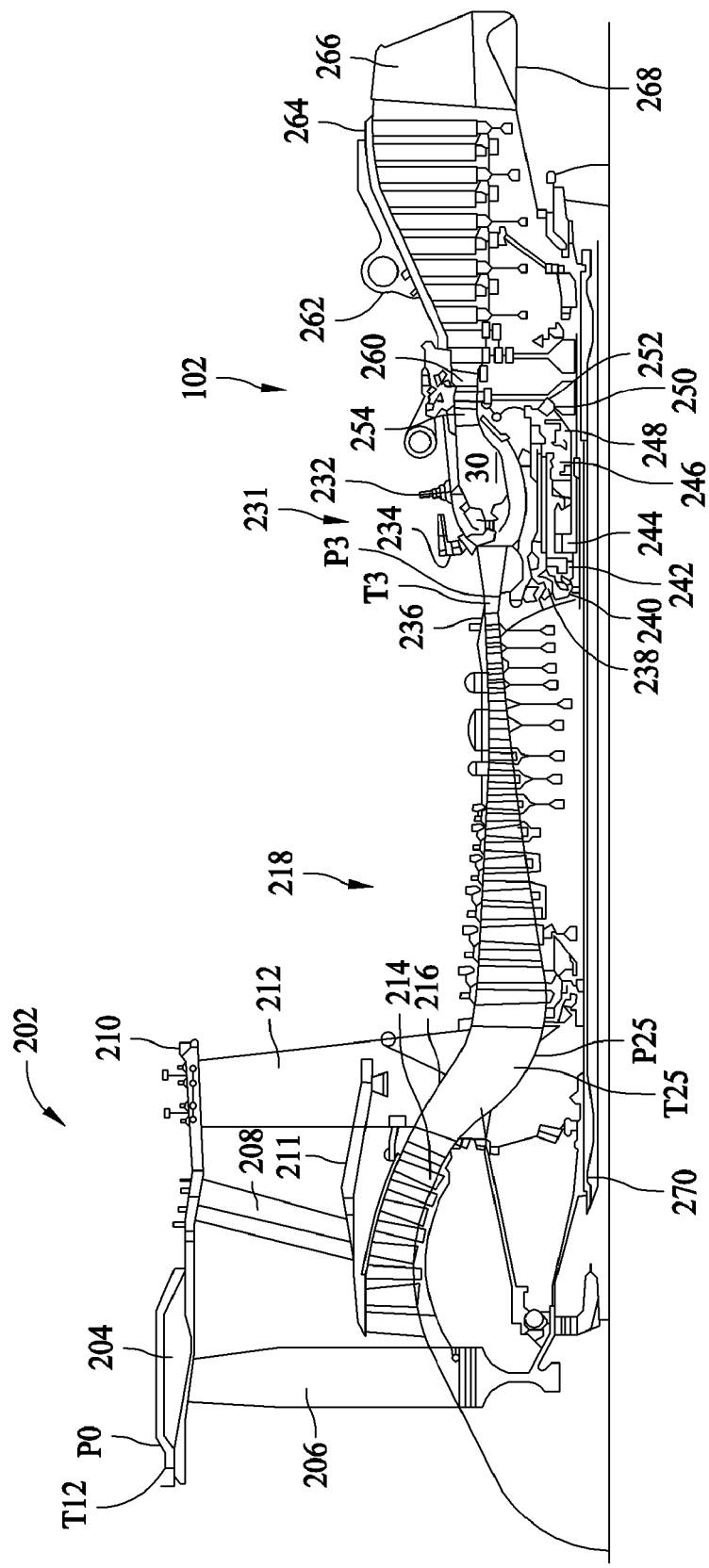
FIG. 2 is cross-sectional view of a gas turbine engine in accordance with an exemplary embodiment of the present invention.

FIG. 2 is cross-sectional view of a gas turbine engine 102 in accordance with an exemplary embodiment of the present invention. Engine 102 includes a fan assembly 202 including a containment 204 and a plurality of fan blades 206. Outlet guide vanes (OGV) 208 extend between aft fan case 210 and an inner casing 211. A fan frame 212 radially supports aft fan case 210. A four stage orthogonal booster 214 co-rotates with fan blades 206. A variable bypass valve (VBV) extends between fan struts 216. Engine 102 includes an engine inlet pressure sensor (P0) and an engine inlet temperature sensor (T12) that measure respective engine process parameters upstream of the fan at the engine inlet, and a compressor inlet temperature (CIT) probe T25 and a compressor inlet pressure port P25 located upstream from a high pressure compressor 218.

A rear frame 231 of compressor 218 includes a combustor 230 and an igniter plug 232 with a fuel nozzle 234 and an outlet guide vane (OGV) 236. It includes a vent seal 238 and 4R/A/O seal 240 and 4R bearing 242 and 4B bearing 244. Rear frame 231 also includes a 5R bearing 246 and 5R/A/O seal 248, a diffuser 250 and pressure balance seal 252. Compressor rear frame 231 also includes a turbine stage 1 nozzle 254. A compressor discharge temperature (T3) sensor and a compressor discharge pressure (P3) port provide access to conditions at the compressor discharge. Engine 102 includes a high pressure turbine 260 and a low pressure turbine 262 that includes a 360° case 264, aerodynamic struts 266 that remove swirl from the exit gas and a turbine rear frame 268 formed as a one piece casting.

In operation, air flows through fan assembly 202 and a first portion of the airflow is channeled through booster 214. The compressed air that is discharged from booster 214 is channeled through compressor 218 wherein the airflow is further compressed and delivered to combustor 230. Hot products of combustion (not shown) from combustor 230 are utilized to drive turbines 260 and 262, and turbine 262 is utilized to drive fan assembly 202 and booster 214 by way of a shaft 270.

Many of the components of engine 102 are monitored by process sensors and structural force sensors that generate signals during various flight modes including initial take-off, level flight and landing. Such signals are relayed via the EEC 108 an on-ground maintenance crew and/or separate remote engine data control center having its own processor.

In the exemplary embodiment, engine inlet pressure (P0) and an engine inlet temperature (T12), compressor discharge temperature (T3) sensor and a compressor discharge pressure (P3) are also used for estimating atmospheric water content. As air traverses the compressor stages of the engine, its pressure and temperature increase. For air containing little water vapor, the value of the specific heat of the air, c, is low. For air containing more water vapor, the value of the specific heat of the air, c is relatively larger. As a result, a temperature rise for moist air flowing through the compressor is less than the temperature rise for dry air flowing through the compressor. For air containing water droplets or ice crystals, overall specific heat, c, is even higher: as the temperature rises, the ice melts and the water vaporizes. Such phase changes absorb large amounts of heat, so the temperature rise in the compressor is even less than the temperature rise for air with a large amount of water vapor.

To convert pressure and temperature measurements into water content, methods of various embodiments of the present invention, for example, use the equations of isentropic compression to compute a ratio of specific heats, a term which is known to those skilled in the art to mean the ratio of $c_P$ (specific heat at constant pressure) to $c_V$ (specific heat at constant volume). The methods then use the ratio of specific heats to determine the water content of the air for example, by using a look-up table.

Figure 3:
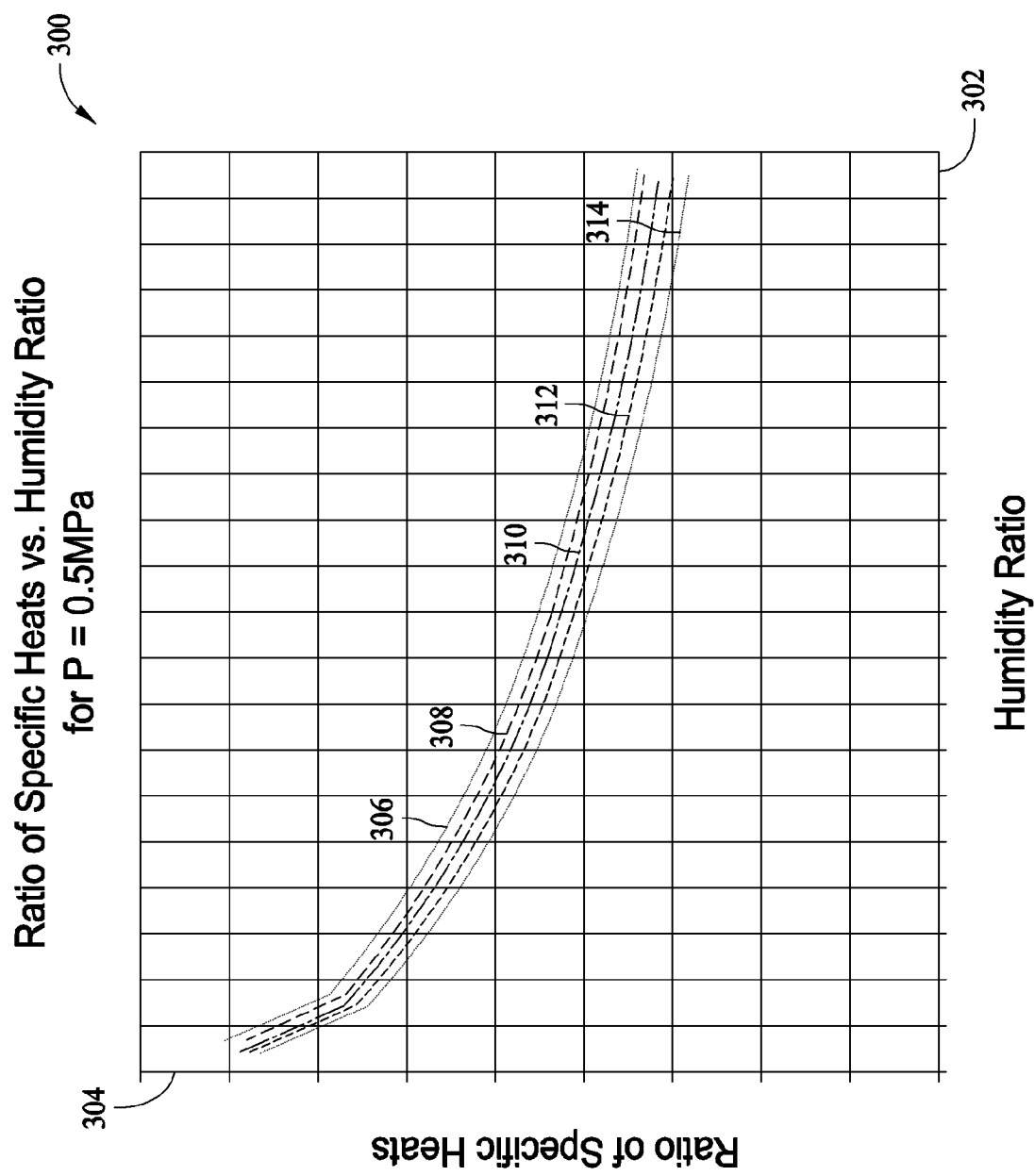
FIG. 3 is a graph of a humidity ratio versus a ratio of specific heats that may be used with system shown in FIG. 1.

FIG. 3 is a graph 300 of a humidity ratio versus a ratio of specific heats that may be used with system 100 (shown in FIG. 1). Graph 300 includes an x-axis 302 graduated in units of humidity ratio and a y-axis 304 graduated in units of a ratio of specific heats. Graph 300 includes a first trace 306 illustrating a relationship between humidity ratio and a ratio of specific heats at a temperature of approximately 180° C. and a pressure of 0.5 MPa. A second trace 308 illustrates a relationship between humidity ratio and a ratio of specific heats at a temperature of approximately 200° C. and a pressure of 0.5 MPa. A third trace 310 illustrates a relationship between humidity ratio and a ratio of specific heats at a temperature of approximately 240° C. and a pressure of 0.5 MPa. A forth trace 312 illustrates a relationship between humidity ratio and a ratio of specific heats at a temperature of approximately 280° C. and a pressure of 0.5 MPa, and a fifth trace 314 illustrates a relationship between humidity ratio and a ratio of specific heats at a temperature of approximately 320° C. and a pressure of 0.5 MPa.

In the exemplary embodiment, engine 102 operates using a Brayton cycle wherein the compression stage is isentropic. For isentropic compression, the following relationship between pressure and absolute temperature applies, where $\gamma$ is the ratio of specific heats ($\gamma = c_p/c_v$):

$$\frac{T_2}{T_1} = \left(\frac{P_2}{P_1}\right)^{1-\frac{1}{\gamma}} \quad (1)$$

If equation (1) is solved for γ, a relationship between humidity and the ratio of specific heats may be applied to determine humidity from measurements of pressure and temperature.

$$\gamma = \frac{\ln\left(\frac{P_2}{P_1}\right)}{\ln\left(\frac{P_2}{P_1}\right) - \ln\left(\frac{T_2}{T_1}\right)} \quad (2)$$

The qualitative relationship between the ratio of specific heats and relative humidity is: as humidity increases, γ decreases. This relationship can be derived from the definition of the ratio of specific heats shown in Equation 3.

$$\gamma = \left(\frac{c_p}{c_v}\right)_{mixture} \quad (3)$$

For an ideal gas, enthalpy, h and internal energy, u can be expressed respectively as:

$$h = c_p T \quad u = c_v T \quad (4)$$

Therefore, the ratio of specific heats can be rewritten as:

$$\gamma = \left[\frac{h/T}{u/T}\right]_{mixture} \quad (5)$$

The temperature term cancels, and the equation can be rewritten using the following relationships for specific enthalpy and specific energy in an air/water vapor mixture, where ω is the humidity ratio.

$$H/m_{air} = h_{air} + \omega \cdot h_{vapor} \quad U/m_{air} = u_{air} + \omega \cdot u_{vapor} \quad (6)$$

The relationship between γ and the humidity ratio becomes:

$$\gamma = \frac{h_{air} + \omega \cdot h_{vapor}}{u_{air} + \omega \cdot u_{vapor}} \quad (7)$$

which, can be solved for the humidity ratio ω as:

$$\omega = \frac{\gamma \cdot u_{air} - h_{air}}{\gamma \cdot u_{vapor} - h_{vapor}} \quad (8)$$

Values for $h_{air}$, $u_{air}$, $h_{vapor}$, and $u_{vapor}$ can be obtained from the ideal gas tables for air and water vapor. FIG. 3 shows the results of the calculation in equation 7 for a representative pressure value of 0.5 MPa. In practice, equation 2 would be used to find γ from temperature and pressure. Then γ would be used to calculate ω via equation 8.

Figure 4:
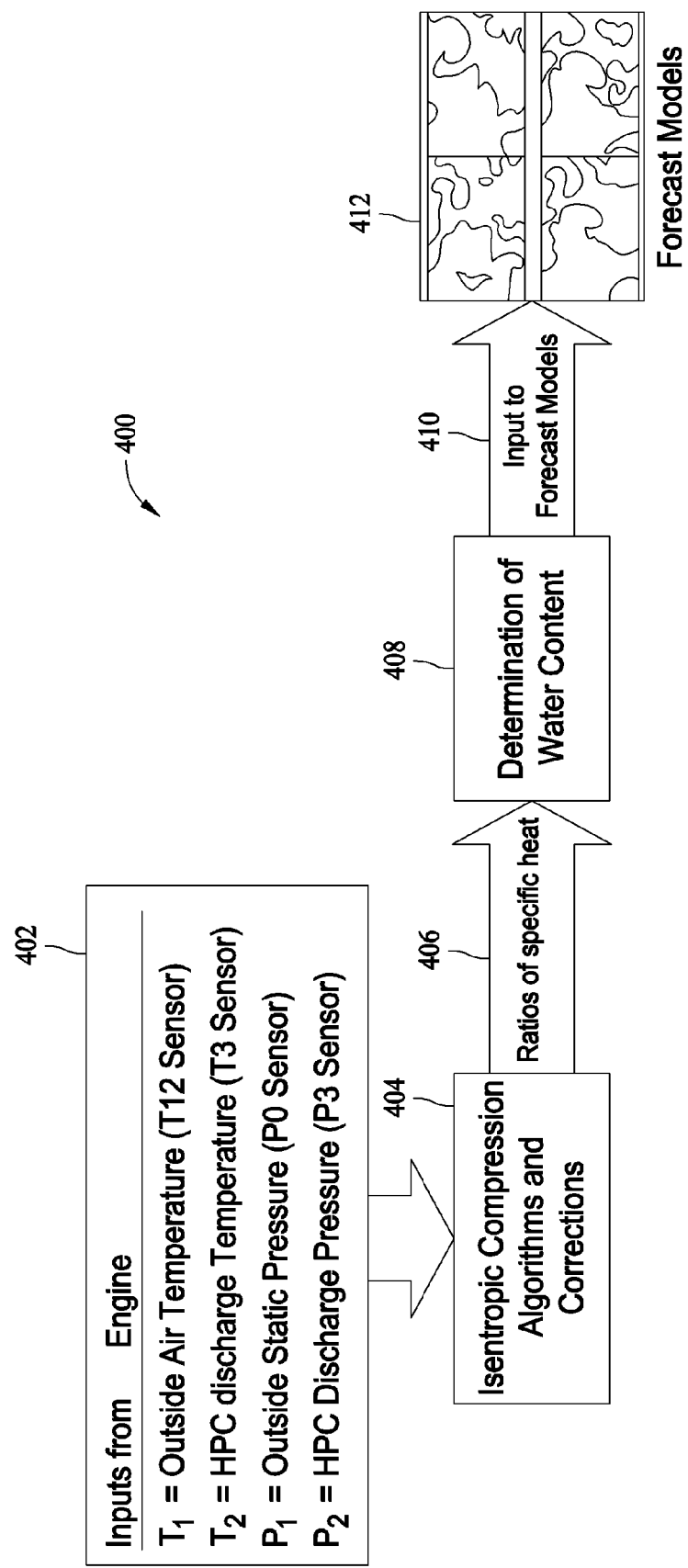
FIG. 4 is a data flow diagram for determining water content in air using measured parameters from a gas turbine engine.

FIG. 4 is a data flow diagram 400 for determining water content in air using measured parameters from a gas turbine engine. A process receives inputs 402 of measured parameters of air temperature and static pressure of the ambient air surrounding for example, the gas turbine engine. The inputs for ambient air temperature and pressure are available from measured parameters from the existing T12 temperature sensor and the P0 pressure sensor, in the exemplary embodiment. In instances where these particular parameters are not measured directly, they may be derived by computing the parameter from other measured parameters. The process also receives inputs 402 of measured parameters of air temperature and static pressure of the compressed air exiting for example, high pressure compressor 218. Such parameters are also measured using existing engine performance sensors, T3 and P3, respectively. By using existing engine performance sensors, new additional sensors are not required to be added to the aircraft and are not mounted in the airstream surrounding the aircraft contributing to additional aircraft drag.

In the exemplary embodiment, T12, P0, T3, and P3 are used in the equations of isentropic compression 404 described above to determine a ratio of specific heats 406 and humidity ratio at the representative pressure and temperature. The processor in the EEC may perform such calculation or the T12, P0, T3, and P3 may be transmitted to a second processor for a determination of the ratio of specific heats and/or humidity ratio. Using the on-board processors or off-board processors to determine the ratio of specific heats and humidity ratio a water content of the air surrounding aircraft 100 is determined 408 in real-time and transmitted to a weather facility where the determined water content is input 410 into weather prediction algorithms to generate forecast models 412 of future weather patterns.

The computations described above can be performed in any of several places: within the Electronic Engine Controller, within another computing device aboard the aircraft, or in a computing device outside the aircraft that receives sensor data transmitted to aircraft 100. The sensor data may be stored aboard the aircraft along with time and location data from the aircraft navigation system so it can be retrieved and used to compute water content after the aircraft lands.

Although the description above refers to the isentropic equations, it is understood the scope of the various embodiments of the present invention includes applying empirical corrections to the computed values to account for non-ideal behavior of the gas, or heat transfers in the engine compressor, which make the process not quite isentropic. Other embodiments of the present invention also include corrections for solid-to-liquid and liquid-to-gas phase changes when the sensed water content exceeds 100% relative humidity at ambient conditions.

Figure 5:
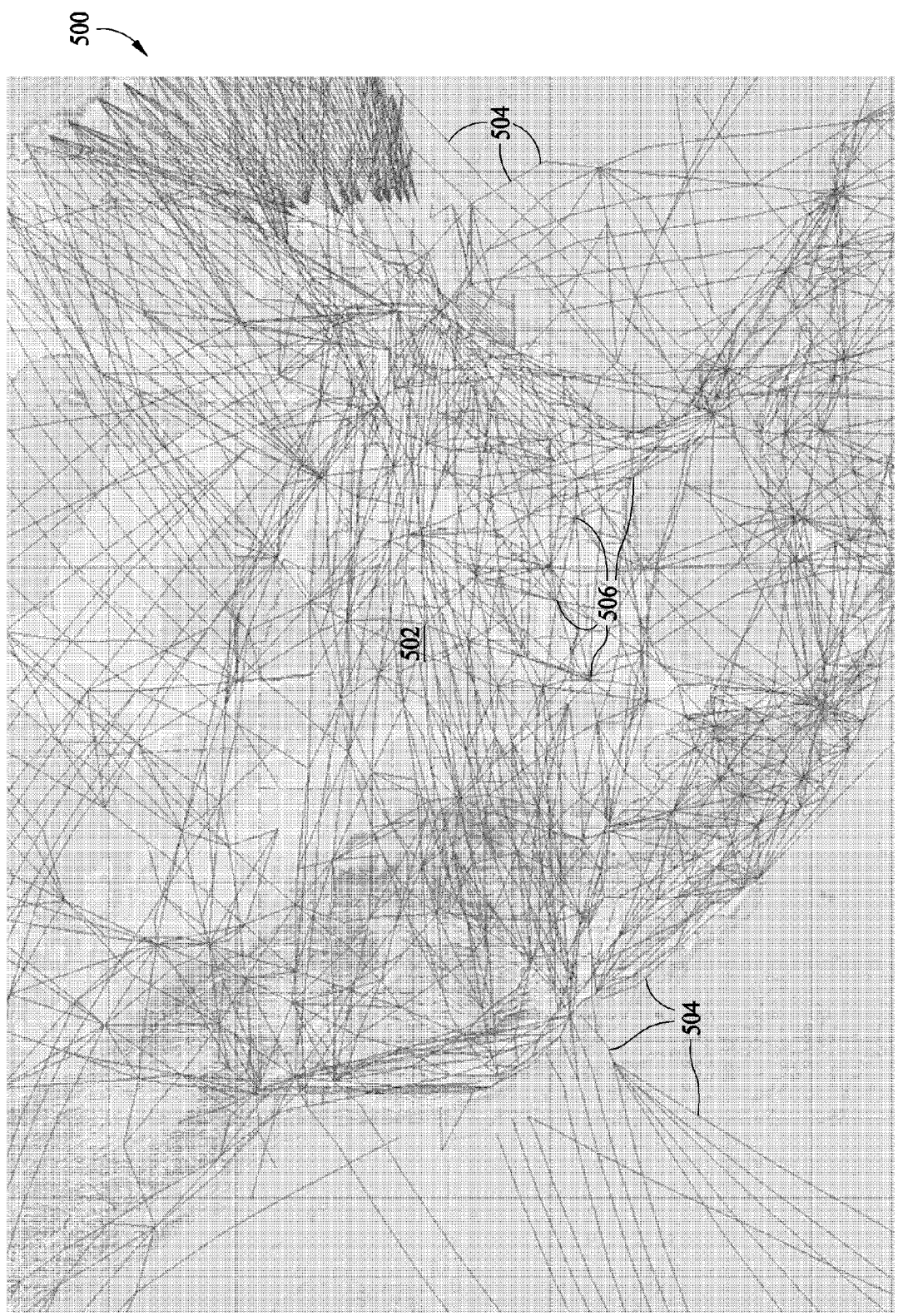
FIG. 5 is a map of the United States illustrating exemplary aircraft routes between various airports which can be used as collection points for weather data in accordance with system shown in FIG. 1.

FIG. 5 is a map 500 of the United States 502 illustrating exemplary aircraft routes 504 between various airports 506 which can be used as collection points for weather data in accordance with system 100 (shown in FIG. 1). Such routes 504 represent the potential data collection coverage for determining water content of the air. In the exemplary embodiment, commercial aircraft enable water content to be continuously measured at low cost along ascents, descents, and routes 504 of flight in the United States 502 and similarly, worldwide. Aircraft traverse such routes multiple times during a given time period increasing the collection of water content data by several orders of magnitude compared to current balloon soundings. Improved water content measurements can substantially improve weather forecasts, with particular improvement for predicting the onset of severe storms driven by convective weather such as those driven by heat released by gas-liquid phase changes in moist air.

Various embodiments of the present invention facilitates real-time and near-real time measurements of water content of the air that are useful for weather forecast models, particularly over the oceans and land masses where few sensors are currently available. Various aircraft operators such as airlines, federal or other national agencies, research institutions, foreign military alliances, and national military air forces benefit from accurate water forecasts for their operation. For oceanic operators such as the Navy or commercial ship operators, inaccurate weather forecasts can lead vessels into unsafe conditions or cause them to take inefficient routes.

The above-described methods and systems for the continuous measurement of atmospheric water vapor by using an aircraft turbine engine as a humidity sensor are cost-effective and highly reliable. Pressure and temperature sensors in the engine's compressor reveal how much the temperature rises as incoming air is squeezed to higher pressure. For air containing more water vapor, the temperature rises less. Measuring the temperature and pressure at two points in the engine compressor permits computing the moisture content of the air. Because modern turbine engines already have appropriate sensors, no modification to existing aircraft engine mechanical systems is required, as only a software modification is necessary, substantially eliminating any weight or drag penalty. Accordingly, the methods and systems facilitate acquisition of weather related data in a cost-effective and reliable manner.

While the invention has been described in terms of various specific embodiments, those skilled in the art will recognize that the invention can be practiced with modification within the spirit and scope of the claims.

What is claimed is:

1. A method for measuring atmospheric water content comprising:
    measuring a first air temperature and a first air pressure at a first location in a compressor;
    measuring a second air temperature and a second air pressure at a second location in the compressor;
    computing a ratio of specific heats from the first and second air temperatures and the first and second air pressures; and
    determining an atmospheric water content from the ratio of specific heats.

2. A method in accordance with claim 1 wherein the compressor is at least one of a portion of a turbine engine and a supercharger.

3. A method in accordance with claim 1 wherein determining an atmospheric water content comprises assuming ideal gas behavior and isentropic compression.

4. A method in accordance with claim 1 wherein determining an atmospheric water content comprises correcting for non-ideal gas behavior.

5. A method in accordance with claim 1 wherein determining an atmospheric water content comprises correcting for non-isentropic compression.

6. A method in accordance with claim 1 wherein measuring a first air temperature and a first air pressure at a first location comprises measuring a first air temperature and a first air pressure at a first location that is upstream from at least one of the compressor and a compressor stage.

7. A method in accordance with claim 1 wherein measuring a second air temperature and a second air pressure at a second location comprises measuring a second air temperature and a second air pressure at a second location that is downstream from at least one of the compressor and a compressor stage.

8. A method in accordance with claim 1 wherein determining an atmospheric water content from the ratio of specific heats comprises using a look-up table.

9. A method in accordance with claim 1 wherein determining an atmospheric water content from the ratio of specific heats comprises using a look-up table relating a ratio of specific heats to a humidity ratio.

10. A method in accordance with claim 1 further comprising:
    recording the time and location of the measurement of at least one of the first air temperature, the second air temperature, the first air pressure, and the second air pressure;
    transmitting each of the measurements, the respective time, and the respective location to a weather forecast model, and
    executing the weather forecast model to generate a weather forecast using the measurement of at least one of the first air temperature, the second air temperature, the first air pressure, and the second air pressure.

11. A method in accordance with claim 10 further comprising providing the weather forecast model with atmospheric measurements from a plurality of times and locations wherein the additional atmospheric measurements are acquired from other than the compressor.

12. A method of forecasting weather comprising:
    determining a specific heat of a volume of air in a gas turbine engine;
    determining a water content of the volume of air using the specific heat of the volume of air;
    transmitting the specific heat and the water content to a weather forecast model; and
    executing the weather forecast model of facilitate generating a weather forecast.

13. A method in accordance with claim 12 wherein determining a specific heat of a volume of air comprises measuring a first air temperature and a first air pressure at a first location.

14. A method in accordance with claim 12 wherein determining a specific heat of a volume of air comprises measuring a second air temperature and a second air pressure at a second location.

15. A method in accordance with claim 12 wherein determining a water content of the volume of air comprises computing a ratio of specific heats from the first and second air temperatures and the first and second air pressures.

16. A method in accordance with claim 12 wherein determining an atmospheric water content from the ratio of specific heats comprises using a lookup table.

17. A method comprising:
    determining a specific heat of a volume of air in a gas turbine engine; and
    determining an atmospheric water content of the volume of air using the specific heat of the volume of air based upon data in a lookup table.

* * * * *